(12) United States Patent
Miyagi et al.

(10) Patent No.: US 7,736,303 B2
(45) Date of Patent: Jun. 15, 2010

(54) CURVILINEARLY CONTROLLING WIRE MEMBER OF ENDOSCOPE AND METHOD FOR MANUFACTURING THE SAME

(75) Inventors: Kunihiko Miyagi, Wako (JP); Masayuki Misawa, Katsushika-ku (JP)

(73) Assignee: Machida Endoscope Co., Ltd., Tokyo (JP)

( * ) Notice: Subject to any disclaimer, the term of this patent is extended or adjusted under 35 U.S.C. 154(b) by 172 days.

(21) Appl. No.: 12/037,741

(22) Filed: Feb. 26, 2008

(65) Prior Publication Data

US 2008/0208003 A1    Aug. 28, 2008

(30) Foreign Application Priority Data

Feb. 26, 2007    (JP) ............... 2007-046066

(51) Int. Cl.
*A61B 1/00* (2006.01)
*D02G 3/00* (2006.01)
(52) U.S. Cl. .................. 600/146; 600/149; 57/224
(58) Field of Classification Search ........... 600/139, 600/141, 142, 144, 146, 149
See application file for complete search history.

(56) References Cited

U.S. PATENT DOCUMENTS 4,677,818 A * 7/1987 Honda et al. .................. 57/224
5,531,664 A * 7/1996 Adachi et al. ............... 600/149

FOREIGN PATENT DOCUMENTS

JP    2001-104239    4/2001

OTHER PUBLICATIONS

Patent Abstracts of Japan publication No. 2001-104239, published Apr. 17, 2001 (1 page).

* cited by examiner

*Primary Examiner*—Linda C Dvorak
*Assistant Examiner*—Alireza Nia
(74) *Attorney, Agent, or Firm*—Osha • Liang LLP

(57) ABSTRACT

A wire member 50 is received in a flexible part 22 of an endoscope 20 and adapted to remotely curvilinearly control a bendable part 27 at a distal end of the flexible insertion part 22. The wire member 50 includes a braid 51 braiding from a plurality of resin fibers and an adhesive agent 52 impregnated in the braid 51 and hardened. The impregnating and hardening of the adhesive agent 52 are carried out in a state where the braid 51 is applied with a tensile force having a predetermined magnitude.

3 Claims, 3 Drawing Sheets

CURVILINEARLY CONTROLLING WIRE MEMBER OF ENDOSCOPE AND METHOD FOR MANUFACTURING THE SAME

TECHNICAL FIELD

This invention relates to a wire member of an endoscope, which wire member is received in a flexible insertion part of the endoscope and adapted to remotely curvilinearly control a bendable part on a distal end of the insertion part, and also to a method for manufacturing the same.

BACKGROUND ART

In general, a soft endoscope is provided with a flexible insertion part. A distal end part of the insertion part is provided as a bendable part consisting of a plurality of joint rings arranged in a row. A single or a plurality of control wires (wire members) are received in the insertion part. A basal end part of the control wire is associated with a control knob of a main body of the endoscope. A distal end part of the control wire is associated with the joint rings arranged in a row on the bendable part. By tensioning the control wire through the control knob, the bendable part can remotely curvilinearly controlled.

Patent Document 1: Japanese Patent Application Laid-Open No. 2001-104239

DISCLOSURE OF THE INVENTION

Problem to be Solved by the Invention

The conventional control wire is formed of a metal wire such as stainless steel. Thus, the wire is narrow and difficult to provide sufficient strength. In addition, the cost is high.

Means for Solving the Problem

In order to solve the above-mentioned problem, the present invention provides a control wire (wire member) composed of resin. According to the present invention, there is provided a remotely curvilinearly controlling wire member of an endoscope, which wire member is received in a flexible insertion part of the endoscope and adapted to remotely curvilinearly control a bendable part of the endoscope on a distal end of the insertion part, the wire member comprising a braid braided from a plurality of resin fibers and an adhesive agent impregnated in the braid and hardened. By impregnation and hardening of the adhesive agent, there can be provided suitable hardness and tension. Thus, even if tensile force is applied at the time of curvilinearly controlling operation, the braid can be prevented from being elongated and deformed.

The resin fiber may be composed of olefin-based resin such as polypropylene and polyethylene, or it may be composed of polyamide-based resin such as nylon.

The braiding means may be any one of the known knitting means, weaving means and twisting means.

It is preferable that the braid includes a main part received in the flexible insertion part and a distal end part passing through a plurality of joint rings arranged in a row on the bendable part, the distal end part being scarcely impregnated with the adhesive agent, or, even if impregnated, in smaller degree of quantity than that impregnated in the main part.

Owing to the above-mentioned arrangement, the braid can be prevented from getting harder at the bendable part than necessary, and the bendable part can be bent smoothly.

The expression "impregnation degree" used herein refers to the "quantity of adhesive agent impregnated per unit length of the braid".

It is preferable that the adhesive agent is impregnated and hardened in a state where the braid is applied with a tensile force having a predetermined magnitude.

According to another aspect of the present invention, there is provided a method for manufacturing a wire member of an endoscope, which wire member is received in an insertion part of the endoscope and adapted to remotely curvilinearly controlling a bendable part at a distal end of the insertion part, the method comprising impregnating an adhesive agent in a braid braiding from a plurality of resin fibers which constitute the wire member; and hardening the adhesive agent while applying a tensile force to the braid.

Owing to the above-mentioned arrangement, the wire member can be uniformed in thickness. The tensile force is preferably set slightly larger than the load acting on the wire member, for example, at the time when the bendable part is curvilinearly controlled.

BEST MODE FOR CARRYING OUT THE INVENTION

One embodiment of the present invention will be described hereinafter.

Figure 1:
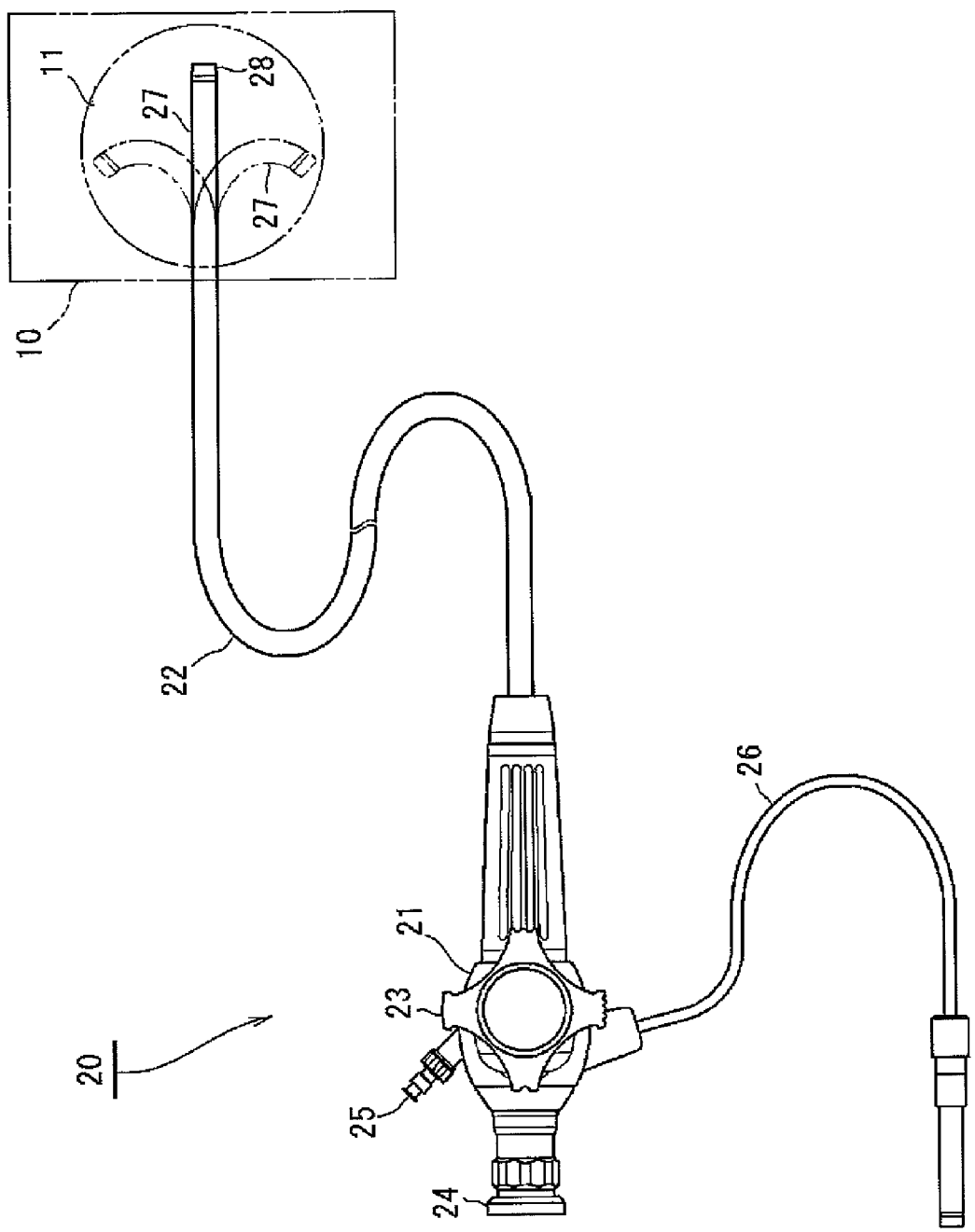
FIG. 1 is a side view showing an overall constitution of a soft endoscope which can be used in combination with an MRI apparatus according to one embodiment of the present invention.

In FIG. 1, reference numeral 10 denotes an MRI apparatus. Reference numeral 20 denotes an endoscope which is, when to be used, inserted in an observation region 11 of the MRI. The endoscope 20 comprises an endoscope main body 21 and an insertion part 22. The endoscope main body 21 is provided at a side part thereof with a control knob 23, at a distal end part thereof with an ocular part 24 and at an upper side part thereof with a forceps introduction part 25. A light guide 26 is led out through a lower side part of the endoscope main body 21 and connected to a light source, not shown. The insertion part 22 extends from a distal end part of the endoscope main body 21. This insertion part 22 is to be inserted into the observation region 11.

Figure 3:
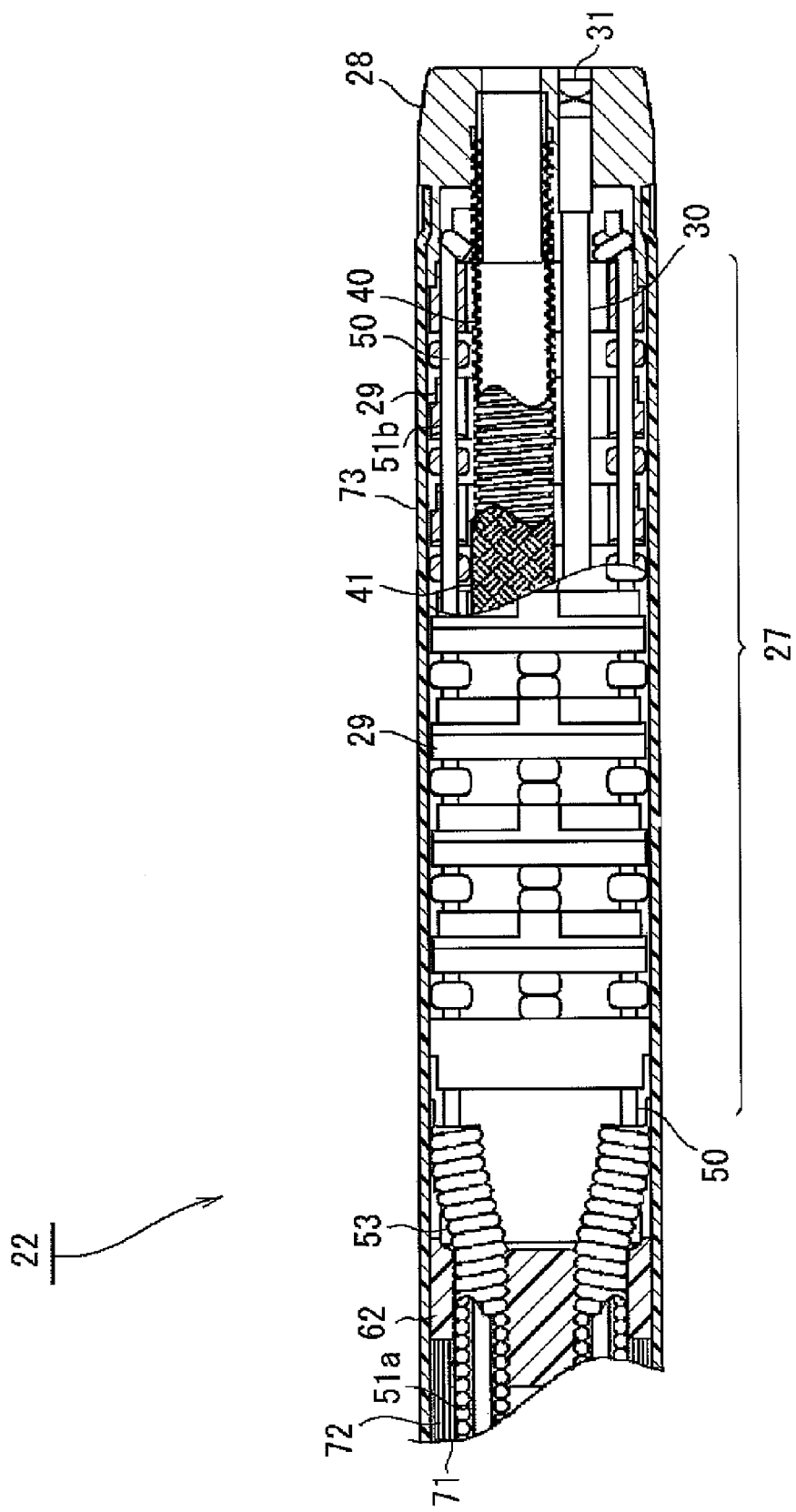
FIG. 3 is a side view showing an internal structure of a distal end part of the insertion part.

As shown in FIGS. 1 and 3, the insertion part 22 is in the form of a flexible tube and includes a bendable part 27 at a distal end part thereof and a tip piece 28 at a further distal end side thereof.

As shown in FIG. 3, the bendable part 27 is provided with a plurality of joint rings 29. Each joint ring 29 is composed of a low magnetic susceptibility material (nonmagnetic member, low magnetic permeability material) such as brass. These joint rings 29 are connected with each other in a row. A distal end part 51b of a curvilinearly controlling wire member 50 (control wire) is passed through the joint rings 29 arranged in a row. By controlling the wire member 50 through the control knob 23, the entire bendable part 27 can be bent (see double-dotted chain line of FIG. 1).

In the Figures, the bendable part 27 is such constructed that it can be bent in two directions. However, it may be such constructed that it can be bent only in one direction or in four directions.

The tip piece 28 is composed of a low magnetic susceptibility material (nonmagnetic material, low magnetic permeability material) such as brass. Gold plating is applied to the surface of the tip piece 28. Gold is the low magnetic susceptibility material (nonmagnetic material, low magnetic permeability material).

Received into the insertion part 22 (including the bendable part 27 and the tip piece 28) are a light guide 26, an image guide 30, a working channel tube 40 and a curvilinearly controlling wire member 50.

The light guide 26 and the image guide 30 are each formed of a bundle of optical fibers which are nonmagnetic members. Though not shown, a distal end of the light guide 26 reaches a distal end face of the tip piece 28. Illumination light from the light source is passed through the light guide 26 to illuminate an object to be observed.

The image guide 30 is provided at a distal end thereof with an objective lens 31. The objective lens 31 is composed of optical glass or plastic, that is a nonmagnetic member. This objective lens 31 is faced with the distal end face of the tip piece 28. An image to be observed is transmitted through the image guide 30 via the objective lens 31 so that the image can be observed by the ocular lens 24.

The working channel tube 40 is composed of resin such as Teflon (Registered Trademark) that is a nonmagnetic member and it has an accordion-shape so that it can provide flexibility. A distal end part of the working channel tube 40 reaches the distal end face of the tip piece 28. For operation, a surgical instrument such as a pair of forceps is inserted into the working channel tube 40 through the forceps introduction part 25 such that it projects from the distal end face of the tip piece 28. An outer peripheral surface of the working channel tube 40 is covered with a mesh tube 41 so that elongation can be restrained. The mesh tube 41 is composed of resin such as Nylon (Registered Trademark) that is a nonmagnetic member.

Figure 2:
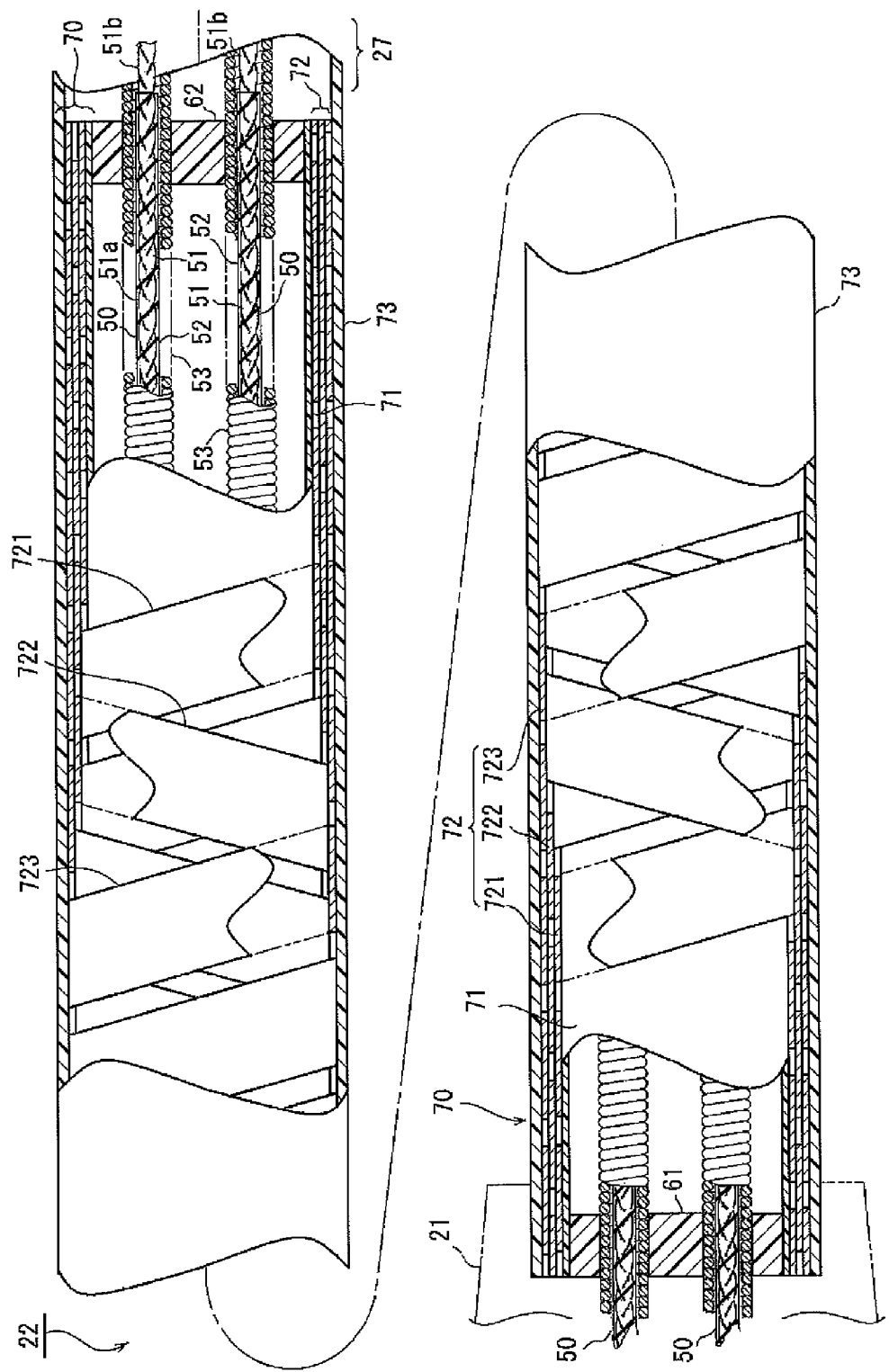
FIG. 2 is a side view showing an internal structure of a flexible portion of an insertion part of the soft endoscope.

As shown in FIGS. 2 and 3, a wire guide 53 is received in a flexible part of the insertion part 22 excluding the bendable part 27 and the tip piece 28. A main part 51a of the curvilinearly controlling wire member 50 is passed through the wire guide 53. The wire guide 53 is formed in a coil-shape, having required elasticity and composed of a low magnetic susceptibility material (nonmagnetic member, low magnetic permeability material). Alloy of copper and silver, for example, is used as a material of the wire guide 53 in this embodiment. Instead of the alloy of copper and silver, phosphor bronze may be used. The distal and basal end parts of the wire guide 53 are secured to a peripheral wall of the insertion part 22 through fixing pieces 61, 62. The fixing pieces 61, 62 are composed of resin that is a nonmagnetic member.

As shown in FIG. 2, a flexible tube 70, which constitutes a peripheral wall (main body part) of the insertion part 22, comprises an internal tube 71, a triple helical tube 72 and an external tube 73. The image guide 30, the light guide 26, the working channel tube 40, the wire guide 53, the curvilinearly controlling wire member 50, etc. are received in the internal tube 71.

The internal tube 71 is composed of resin that is a nonmagnetic member. Resin having not only flexibility but also sufficient tensile force and compression strength is preferable as a resin material composing the internal tube 71. The resin of this type is preferably an olefin-based resin such as polyethylene and polypropylene. As a resin material composing the internal tube 71, polyethylene (Irrax Registered Trademark) manufactured by Sumitomo Electric Industries, Ltd.), for example, is used in this embodiment.

Instead of polyethylene, other polyolefin-based resin such as polypropylene may be used as a resin material composing the internal tube 71. In another preferable alternative, a polyamide-based resin such as nylon can be listed. Other resin materials may also be used.

The outside of the internal tube 71 is covered with the triple helical tube 72. The triple helical tube 72 comprises a first helical band 721, a second helical band 722 and a third helical band 723. Those first through third helical bands 721, 722, 723 are each composed of a band having a helical shape. The first helical band 721 is tightly wound around an outer peripheral surface of the internal tube 71. The second helical band 722 is tightly wound around an outer peripheral surface of the first helical band 721. The winding direction of the second helical band 722 is reversed to the winding direction of the first helical band 721. The third helical band 723 is tightly wound around an outer peripheral surface of the second helical band 722. The winding direction of the third helical band 723 is reversed to the winding direction of the second helical band 722 and same as the winding direction of the first helical band 721. Both ends of the triple helical tube 72 are sandwiched and fixed between the fixing pieces 61, 62 and the external tube 73.

The first through third helical tubes 721 through 723 are provided with required elasticity and tensile force, and in addition, they are composed of a low magnetic susceptibility material (nonmagnetic member, low magnetic permeability material). Phosphor bronze is used as material of the first through third helical bands 721, 722, 733 in this embodiment. Instead of phosphor bronze, alloy of copper and silver may be used. The phosphor bronze and the alloy of copper and silver can fully satisfy the above-mentioned required physical properties.

Instead of nonmagnetic metal (alloy) such as phosphor bronze and alloy of copper and silver, resin such as polypropylene and polyethylene may be used as material of the first through third helical bands 721, 722, 723.

The external tube 73 is composed of resin such as polypropylene and polyethylene that is a nonmagnetic member. The outside diameter of the external tube 73 is 10 mm or less, for example, about 7 mm. The external tube 73 is provided not only to the flexible part of the insertion part 22 but also to the bendable part 27 and it reaches the tip piece 28.

The curvilinearly controlling member 50 will be described in detail.

The curvilinearly controlling member 50 is obtained by impregnating an adhesive agent 52 in a braid 51 and hardening the adhesive agent 52. The adhesive agent 52 is a nonmagnetic member. The braid 51 is obtained by braiding resin fibers which each is a nonmagnetic member. As a resin fiber composing the braid 51, an olefin-based resin such as polypropylene and polyethylene is used in this embodiment. There is no limitation to the braiding method, and various methods, such as knitting, weaving and twisting may be employed.

The adhesive agent 52, which is to be impregnated in the braid 51, can be selected from a wide variety of adhesive agents and it may be a commercially available one such as, for example, Cianobond (Registered Trademark).

Impregnation is carried out while tensioning the braid 51. The tensile force may be set slightly larger than a load (about 2 kgf) which acts on the curvilinearly controlling member 50 at the time when the bendable part 27 is subject to the curvilinearly controlling operation.

One example of the braiding method is as follows. A weight corresponding to the above-mentioned load is tied to one end of the braid 51 and hung therefrom. The adhesive agent 52 is dropped into the braid 51 through an upper end part thereof. The adhesive agent 52 permeates into the meshes of the braid 51 and is impregnated in the braid 51. The tensile force is preferably kept applied to the braid 51 until the adhesive agent 52 is hardened.

Impregnation and hardening of the adhesive agent 52 provides suitable hardness and tension to the braid 51.

The adhesive agent 52 is impregnated in the braid 51 excepting the distal end part (second part) 51b received in the bendable part 27. Namely, the adhesive agent 52 is impregnated in the portion received in the endoscope main body 21 of the braid 51 and the main part (first part) 51a received in the internal tube 71 of the braid 51.

The braid distal end part 51b received in the bendable part 27 is not impregnated with the adhesive agent 52.

According to this soft endoscope 20, the various component members of the insertion part 22 are each composed of a nonmagnetic member. By virtue of this arrangement, even if the insertion part 22 is arranged at the observation region 11 of the MRI, the magnetic field of the MRI is not heavily disturbed. Accordingly, disturbance to observation of the MRI can be restrained or prevented. Owing to this feature, operation, etc. can be carried out by the soft endoscope 20 while observing the MRI.

Owing to the provision of the internal tube 71 and the triple helical tube 72, various strengths required for the insertion part 22, such as tension, compression and twisting, can sufficiently be born. More particularly, owing to the provision of the internal tube 71, tensile force and compression strength can be born, and owing to the provision of the triple helical tube 72, twisting strength can be born. Moreover, in case the flexible insertion part 22 is bent, the sectional configuration of the internal tube 71 can be maintained by the triple helical tube 72 at the bendable part and thus, it can be prevented that the internal tube 71 yields and the section is crushed.

As mentioned above, since the internal tube 71 can be supplemented in strength by the triple helical tube 72, the outside diameter of the internal tube 71 can be minimized as much as possible and the tube wall of the internal tube 71 can be minimized in thickness as much as possible. By virtue of this, the insertion part 22 can be minimized as much as possible so that the patient's burden can be reduced.

Since the curvilinearly controlling wire member 50 is formed of the braid 51 which is composed of resin fibers, it can be manufactured at a lower cost than the metal wire which is formed of stainless steel or the like. By impregnating and hardening the adhesive agent 52 in the braid 51, the resin-made bendable wire 50 can be prevented from being elongated even if tensile force is applied thereto at the time when the bendable part 27 is curvilinearly controlled.

By impregnating and hardening the adhesive agent 52 while tensioning the braid 51, the curvilinearly controlling wire member 50 can be uniformed in thickness.

Since no adhesive agent 52 is impregnated in the braid distal end part 51b which is received in the bendable part 27, the bendable part 27 can be bent easily.

The present invention is not limited to above-mentioned embodiment but it can be changed and modified within a spirit and scope of the disclosure.

For example, the endoscope 20 of the above-mentioned embodiment is used in combination with the MRI. However, the curvilinearly controlling wire member according to the present invention is not limited to this, but it can also be widely applicable to the normal endoscope wherein there is no necessity to take into account the magnetic field.

Instead of polyolefin-based resin such as polypropylene and polyethylene, polyamide-based resin such as nylon may be used as the resin fiber composing the braid 51 of the curvilinearly controlling wire member 50.

The method for impregnating the adhesive agent 52 in the braid 51 is not limited to the disclosure mentioned above.

Instead of the arrangement wherein the tensile force applied to the braid 51 at the time when the adhesive agent is impregnated and hardened is set slightly larger than the load acting on the curvilinearly controlling wire member 50 at the time when the bendable part 27 is curvilinearly controlled, the tensile force may be set almost equal to or larger enough than the load. Likewise, the tensile force may be set smaller than the load and the adhesive agent 52 may be impregnated without tensioning the braid 51.

The adhesive agent 52 may also be impregnated in the braid distal end part 51b received in the bendable part 27. The impregnation degree of the adhesive agent 52 into the braid distal end part 51b may be set smaller than that of the adhesive agent 52 into the main part 51a.

Instead of nonmagnetic metal (alloy) such as alloy of copper and silver and phosphor bronze, resin such as polypropylene and polyethylene may be used as the wire guide 53. In case the present invention is applied to the normal endoscope wherein there is no necessity to take into account the magnetic field, the wire guide 53 may be composed of metal having a comparatively high magnetic susceptibility (magnetic permeability) such as stainless steel.

INDUSTRIAL APPLICABILITY

The present invention can be applied to a soft endoscope having a flexible insertion part.

The invention claimed is:

1. A remotely curvilinearly controlling wire member of an endoscope, which the wire member is adapted to remotely control a plurality of joint rings arranged in a row of a bendable part of the endoscope on a distal end of a flexible insertion part of the endoscope, the wire member comprising:
a braid braided from a plurality of resin fibers, the braid being received in the insertion part and in the joint rings; and an adhesive agent impregnated in the braid and hardened, the impregnation degree of the adhesive agent being relatively higher at a first part of the braid received in the insertion part and relatively lower or zero at a second part of the braid received in the joint rings.

2. A remotely curvilinearly controllable endoscope comprising:
a flexible tubular insert part;
a bendable part having a plurality of joint tings arranged in a row and being continuous to a distal end of the insertion part and a wire member adapted to remotely control the joint rings, the wire member including a braid braided from a plurality of resin fibers and an adhesive agent impregnated in the braid and hardened, wherein the braid is received in the flexible insertion part and in the joint rings, and wherein the impregnation degree of the adhesive agent is relatively higher at a first part of the braid received in the insertion part and relatively lower or zero at a second part of the braid received in the joint rings.

3. A method for manufacturing a remotely curvilinearly controllable endoscope, including an insertion part, a bendable part having a plurality of joint rings arranged in a row at a distal end of the insertion part and a wire member adapted to remotely control the bendable part, the method comprising:
impregnating an adhesive agent in a braid as the wire member braiding from a plurality of resin fibers in such a way that the impregnation degree of the adhesive agent is relatively higher at a first part of the braid and relatively lower or zero at a second part continuous to an end of the first part of the braid while applying a tensile force to the braid; hardening the adhesive agent while maintaining the tensile force applying to the braid; and disposing the first part having a higher impregnation degree in the insertion part and the second part having a lower or zero impregnation degree in the joint rings.

* * * * *